United States Patent [19]

Caplan et al.

[11] Patent Number: 4,620,327
[45] Date of Patent: Nov. 4, 1986

[54] PROCESS OF ADAPTING SOLUBLE BONE PROTEIN FOR USE IN STIMULATING OSTEOINDUCTION

[76] Inventors: Arnold I. Caplan, 1300 Oakridge Dr., Cleveland Heights, Ohio 44121; Glenn T. Syftestad, 3660 Warrensville Center Rd. #101, Shaker Heights, Ohio 44122

[21] Appl. No.: 628,168

[22] Filed: Jul. 5, 1984

[51] Int. Cl.$^4$ ..................... A01N 63/02; A61K 35/32
[52] U.S. Cl. ......................................... 632/10; 424/95; 514/2; 514/21; 623/16
[58] Field of Search ................... 3/1.9; 424/95; 514/2, 514/21

[56] References Cited

U.S. PATENT DOCUMENTS

| | | | |
|---|---|---|---|
| 4,394,370 | 7/1983 | Jefferies | 3/1.9 |
| 4,430,760 | 2/1984 | Smestad | 3/1.9 |
| 4,440,750 | 4/1984 | Glowacki et al. | 424/95 |
| 4,472,840 | 9/1984 | Jefferies | 3/1.9 |
| 4,526,909 | 7/1985 | Urist | 424/95 |

*Primary Examiner*—Morton Foelak
*Assistant Examiner*—Kriellion Morgan
*Attorney, Agent, or Firm*—Watts, Hoffman, Fisher & Heinke Co.

[57] ABSTRACT

A method for treating implants such as biodegradable masses, xenogenic bony implants, allografts and prosthetic devices with soluble bone protein to enhance or stimulate new cartilage and/or bone formation. Substrate immobilization or surface coating techniques retard diffusion of the soluble bone protein away from the implant site so that cartilage and bone growth is initiated.

12 Claims, No Drawings

PROCESS OF ADAPTING SOLUBLE BONE PROTEIN FOR USE IN STIMULATING OSTEOINDUCTION

DESCRIPTION

1. Technical Field

This invention relates generally to a method for stimulating osteoinduction and more specifically to a process for adapting soluble 'regenerating' factors to effectively initiate new cartilage and/or bone growth at selected skeletal locations in humans and animals.

2. Background Art

Regeneration of skeletal tissues is regulated by specific protein factors that are naturally present within bone matrix. During the healing process, these components stimulate certain cell populations to form new cartilage and bone tissue which serve to replace that which was lost or damaged. Such protein substances, if extracted and purified, have potential use in clinical situations where skeletal tissue regeneration is necessary to restore normal function, for example, at fracture sites and at sites of periodontal defects. In addition, such a protein substance can enhance or promote bony ingrowth into various prosthetic devices and bony implants, such as allografts, processed xenogenic bone chips and the like.

Bone matrix protein is readily soluble in body fluids. Its solubility precludes direct in vivo implantation at the site of a skeletal defect. For example, if a dissolvable capsule containing soluble bone protein is implanted at an ectopic intra-muscular site, no cartilage or bone induction occurs. Similarly no cartilage or bone induction occurs when soluble bone protein is incorporated, by lyophilization, into an inert carrier (i.e., demineralized guanidinium chloride extracted cancellous or cortical bone chips) and implanted at ectopic sites. Diffusion of such soluble proteins away from the implant site occurs before the 1-2 days necessary for appropriate cell populations to accumulate. Thus, special procedures are required to 'immobilize' this substance in such a way that factor release coincides with the presence of sufficient numbers of responsive cell types which then will be stimulated to form cartilage and bone.

DISCLOSURE OF THE INVENTION

This application is related to copending application Ser. No. 591,505, under the title of Bone Purification Process, which discloses a process of obtaining a soluble bone matrix derived protein capable of causing undifferentiated cells to undergo chondrogenesis and to copending application Ser. No. 591,440, under the title of Process of and Material for Stimulating Growth of Cartilage and Bony Tissue at Anatomical Sites, which discloses a process in which live cells are exposed in vitro to the bone protein and then transferred in vivo to cause chondro/osteogenesis. The disclosures of both copending applications are incorporated by reference.

The invention provides a method of adapting soluble bone protein for use in osteoinduction and involves combining soluble bone protein purified to a state effective to initiate chondrogenesis with carrier means for retarding diffusion of said protein from a site of in vivo implantation.

In one embodiment of the invention, the carrier means for retarding diffusion of soluble bone protein comprises a biocompatible, biodegradable mass capable of releasing the protein in a time dependent manner. A preferred carrier of this class is a fibrin clot. A fibrin clot is useful in that it can be molded to fit the contours of small defects such as periodontal pockets.

In another embodiment the carrier means comprises bony implant means such as allografts, specially processed xenogenic bone chips and the like, treated so as to be capable of releasing the protein in a time dependent manner. The bony implant means can be treated by soaking in a surface coating solution, such as a gelatin or fibrin solution or the like, that is capable of being dried to form an adherent, biodegradable coating. Another method of immobilization involves chemical cross-linking of inert carriers into which soluble bone matrix derived protein has been incorporated. Both techniques are effective to trap the soluble bone protein and to provide for its controlled release when implanted in vivo.

A preferred procedure involving demineralized, defatted, 4M guanidinium chloride extracted bone, which is typically 90% Type I collagen, comprises soaking the bone in a solution of the soluble bone protein, drying the bone, and then cross-linking it with agents such as gluteraldehyde, formaldehyde, carbodiimide or the like. The cross-linking procedure effected by these agents results in a molecular collapse of the collagenous matrix structure thereby trapping incorporated soluble bone protein. Such physical entrapment within this insolubilized matrix increases the time normally required for matrix hydration by interstitial fluid so that protein release is sufficiently prolonged to allow for adequate host tissue ingrowth.

Another embodiment of the invention which is particularly applicable to prosthetic devices comprises the steps of soaking the prosthesis in a surface coating solution containing soluble bone protein purified to a state effective to initiate chondrogenesis and a controlled release agent. The surface coating is dried on the prosthesis so as to form an adherent insolubilized coating capable of releasing the protein in a time dependent manner. The controlled release agent is at least one member selected from the group consisting of gelatin and fibrin, with gelatin being preferred. The gelatin-bone protein coating, which can be applied to a variety of prosthetic devices to initiate cartilage and bone formation at the tissue-implant interface, is insolubilized directly upon the implant by simple dehydration. The relatively insoluble nature of the dehydrated complex prolongs protein release for the appropriate period. Fixation of steel, ceramic and other metal alloy implant devices used for reconstruction or stabilization of damaged bone will be enhanced through the stimulation of a natural osseous bridge anchoring the implant within the surrounding skeletal tissue.

Other features and a fuller understanding of the invention will be had from the following detailed description of the best modes.

BEST MODES FOR CARRYING OUT THE INVENTION

The following examples more fully describe the invention useful for regenerating skeletal tissue by enhancing bone ingrowth into bone defects, bony implants and prosthetic devices.

EXAMPLE I

An intended use for the method of the present invention involves the direct implantation into fracture sites or periodontal defects of treated bone into which soluble bone protein has been incorporated.

Bovine cancellous bone chips were demineralized in 0.6M HCl for 4 days at 4° C. Following a cold (4° C.) water wash, the bone pieces were defatted in chloroform-methanol (1:1) at room temperature and allowed to air dry overnight. A 4M guanidinium chloride extraction (3 days at 4° C.) removed soluble components possessing interfering biological or immunological properties. The bone pieces were then lyophilized.

Small square shaped pieces (4–5 mm Long × 1–2 mm wide) of the demineralized, defatted bone were incubated under vacuum in an aqueous solution containing 800–1000 ugs Lowry protein/ml of soluble bone protein identified as Protein $A_{VI}$, prepared in accordance with the process disclosed in Ser. No. 591,505. One such treated bone piece absorbed approximately 200 ul of solution, thereby incorporating about 200 ug of soluble bone protein. Because the treated bone piece had a highly porous structure, the surface area could not be accurately determined, but was estimated to be 2–3 cm$^2$, which gave a coating concentration of roughly 60–100 ug/cm$^2$. The bone pieces were lyophilized. Some of them were further treated by cross-linking with gluteraldehyde (2.5% in water) at 4° C. overnight. Excess gluteraldehyde was removed with a cold water rinse.

Other small pieces of the demineralized defatted bone were soaked in a 10% gelatin solution containing 800 ug/ml of Protein $A_{VI}$. These were air dried overnight so as to coat the external surfaces of the carrier with a thin layer of semi-solid gelatin-bone protein mixture. A 10% gelatin solution solidifies at 25° C. and progressively dehydrates with time forming first a viscous glue and finally a dry adherent paste.

EXAMPLE 2

Soluble bone protein identified as Protein $A_{VI}$ was prepared in accordance with the procedure disclosed in Ser. No. 591,505. 800 to 100 ug Protein $A_{VI}$ was added to 1 ml of 0.1phosphate buffer (ph 7.4) containing 50 mg fibrinogen. To this mixture was added 20 units of thrombin (20 ul of a 1000 units/ml stock solution). Within several minutes a clot formed, trapping Protein $A_{VI}$ inside the clot.

The clot was implanted into a defect in the illiac crest of adult Fischer rats. This defect was created by removing a standarized section (0.5 cm) of crest bone from the illium using a pair of roungers. Three to four weeks after implantation, the site of the implant was assessed histologically. Defect sites implanted with fibrin clots containing soluble bone protein showed increased amounts of cartilage or bone formation compared to the amounts of cartilage or bone formed at defect-sites implanted with fibrin clots containing albumen or with fibrin clots alone.

EXAMPLE 3

Demineralized bone chips prepared as described in Example 1, (4 to 5 mm long; 1 to 2 mm wide) were incubated in a 10% gelatin solution containing 800 ug/ml of the Protein $A_{VI}$. The treated bone chips were air dried and implanted at an ectopic intra muscular site in five to eight week old CBA male mice. Fourteen days after implantation, sites were examined by X-ray and histology. Sites implanted with gelatin-soluble bone protein coated chips showed induction of cartilage and bone. Sites implanted with gelatin-albumen coated chips showed no induction.

EXAMPLE 4

Demineralized bone chips prepared as described in Example 1 were incubated under vacuum in an aqueous solution containing 800–1000 ug/ml of Protein $A_{VI}$. The chips were cross-linked by soaking overnight in a 2.5% solution of gluteraldehyde at 4° C. The chips were implanted into ectopic intra-muscular sites as in Example 3. Fourteen days after implantation, the sites were examined by X-ray and histology. Sites implanted with cross-linked bone protein chips showed induction of cartilage and bone formation. Sites implanted with cross-linked albumen chips showed no induction.

EXAMPLE 5

Human bone chips demineralized and defatted as described in Example 1 were incubated under vacuum in an aqueous solution containing 800–1000 ug/ml of Protein $A_{VI}$. The chips were cross-linked with gluteraldehyde as in Example 4 were implanted in an ectopic sub-cutaneous site in white leghorn chick hatchlings. Fifteen days after implantation the sites were examined histologically. Sites implanted with cross-linked bone protein chips showed cartilage and bone deposits. Sites implanted with cross-linked albumen chips showed fibrous encapsulation only.

Modifications of the above invention and materials and procedures employed therein which are obvious to persons of skill in the art are intended to be within the scope of the following claims.

We claim:

1. A method of adapting soluble bone protein for use in osteoinduction comprising combining soluble bone protein purified to a state effective to initiate chondrogenesis with a biocompatible, biodegradable mass capable of releasing the protein in a time dependent manner for retarding diffusion of said protein from a site of in vivo implantation.

2. A method of adapting soluble bone protein for use in osteoinduction comprising combining soluble bone protein purified to a state effective to inititate chondrogenesis with a fibrin clot for retarding diffusion of said protein from a site of in vivo implantation.

3. A method of adapting soluble bone protein for use in osteoinduction comprising the steps of soaking an allograft in an aqueous solution of a controlled release agent and soluble bone protein purified to a state effective to initiate chondrogenesis, and drying the allograft to form an adherent coating capable of releasing the protein in a time dependent manner.

4. A method of adapting soluble bone protein for use in osteoinduction comprising the steps of soaking demineralized, defatted bone, extracted to remove biological or immunological properties, in an aqueous solution of bone protein purified to a state effective to initiate chondrogenesis, and cross-linking the treated bone so that it is capable of releasing the protein in a time dependent manner.

5. A method of adapting soluble bone protein for use in osteoinduction comprising the steps of soaking a prosthesis in a surface coating solution of a controlled release agent and bone protein purified to a state effective to initiate chondrogenesis and drying the prosthesis to form an adherent coating capable of releasing the protein in a time dependent manner.

6. The method of claim 3 wherein the controlled release agent is at least one member selected from the group consisting of gelatin and fibrin.

7. The method of claim 5 wherein the controlled release agent is at least one member selected from the group consisting of gelatin and fibrin.

8. A method of adapting soluble bone protein for use in osteoinduction comprising combining soluble bone protein purified to a state effective to initiate chondrogenesis with bony implant means and a surface coating solution capable of being dried to form an adherent biodegradable coating capable of releasing the protein in a time dependent manner for retarding diffusion of said protein from a site of in vivo implantation.

9. The method of claim 8 wherein the surface coating solution is a solution of at least one member selected from the group consisting of gelatin and fibrin.

10. A method of adapting a soluble bone protein for use in osteoinduction comprising combining soluble bone protein purified to a state effective to initiate chondrogenesis with bony implant means and thereafter cross linking said bony implant means so that it is capable of releasing the protein in a time dependent manner for retarding diffusion of said protein from a site of in vivo implantation.

11. A method of adapting soluble bone protein for use in osteoinduction comprising combining soluble bone protein purified to a state effective to initiate chondrogenesis with a prosthesis and a surface coating solution capable of being dried to form an adherent biodegradable coating so that it is capable of releasing the protein in a time dependent manner for retarding diffusion of said protein from a site of in vivo implantation.

12. The method of claim 11 wherein said surface coating solution is a solution of at least one member selected from the group consisting of gelating and fibrin.

* * * * *